United States Patent
Erkkilä

(10) Patent No.: US 7,092,751 B2
(45) Date of Patent: Aug. 15, 2006

(54) DETECTION OF ATRIAL ARRHYTHMIA

(75) Inventor: Jouni Erkkilä, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 481 days.

(21) Appl. No.: 10/668,671

(22) Filed: Sep. 23, 2003

(65) Prior Publication Data

US 2005/0065444 A1    Mar. 24, 2005

(51) Int. Cl.
*A61B 5/04* (2006.01)

(52) U.S. Cl. ........................ 600/515; 600/509

(58) Field of Classification Search ................ 600/509, 600/515; 607/17
See application file for complete search history.

(56) References Cited

U.S. PATENT DOCUMENTS

| | | | |
|---|---|---|---|
| 6,064,906 A | 5/2000 | Langberg et al. | |
| 6,144,878 A * | 11/2000 | Schroeppel et al. | ........ 600/515 |
| 6,178,347 B1 | 1/2001 | Olsson | |
| 6,442,429 B1 | 8/2002 | Hill et al. | |
| 6,449,503 B1 | 9/2002 | Hsu | |
| 6,470,210 B1 | 10/2002 | Chen et al. | |
| 6,490,479 B1 | 12/2002 | Bock | |
| 6,511,500 B1 * | 1/2003 | Rahme | ........................ 607/1 |

OTHER PUBLICATIONS

Ventricular response in atrial fibrillation: random or deterministic?, Kenneth M. Stein, et al., 1999 The American Physiological Society, pp. H452-H458.

Autonomic Assessment Report, A Comprehensive Heart Rate Variability Analysis, Interpretation Guide and Instructions, Rollin McCraty et al., 1996 Institute of HeartMath, pp. 1-42.

* cited by examiner

*Primary Examiner*—Robert E Pezzuto
*Assistant Examiner*—Brian T. Gedeon
(74) *Attorney, Agent, or Firm*—Andrus, Sceales, Starke & Sawall, LLP

(57) ABSTRACT

The invention relates to a method and system for detecting atrial arrhythmia, especially atrial fibrillations. Based on at least one electrical signal indicative of a heart's activity, a plurality of short-term HRV data sets are generated, one short-term HRV data set indicating the heart's rate variability within a time period of a given length, and two consecutive short-term HRV data sets having a given time difference. A frequency analysis of each short-term HRV data set is then performed and a power level corresponding to at least one selected frequency component in each short-term HRV data set is defined. The occurrence of the heart's atrial arrhythmia episodes are then estimated on the basis of the power levels defined.

24 Claims, 4 Drawing Sheets

DETECTION OF ATRIAL ARRHYTHMIA

FIELD OF THE INVENTION

The present invention relates generally to a method and system for detecting atrial arrhythmia, especially atrial fibrillation. The invention is primarily intended for continuous patient monitoring in acute care.

BACKGROUND OF THE INVENTION

The normal cardiac cycle includes contractions of the atrial muscles, which are activated by the autonomic sinoatrial node (SA node), also called the sinus node. The electrophysiologic (EP) signal generated by the SA node spreads in the right and left atrium leading to their contraction. The EP signal further reaches the atrioventricular node (AV node) situated between the atria and the ventricles. The AV node delays the EP signal, giving the atria time to contract completely before the ventricles are stimulated. After the delay in the AV node the EP signal spreads to the ventricles via the fibers of the His-Purkinje system leading to the contraction of the ventricles. After the contraction the atria are relaxed and filled by blood coming from venous return. The entire cardiac cycle is the combination of atrial and ventricular contraction, i.e. depolarization, and their relaxation, i.e. repolarization.

As is known, the cardiac cycle can be measured non-invasively by attaching small electrodes on the skin of the patient. The voltage differences caused by the heart between the electrodes are measured and recorded in order to obtain the electrocardiogram (ECG) of the patient.

In this connection, reference is made to FIG. 1, which shows one cycle of an ECG signal. As is commonly known, and also shown in the figure, the waves of the ECG signal (i.e. the depolarisation and repolarisation events in the heart) are named alphabetically from P to U. The ECG signal shows each phase of the cardiac cycle: the P wave represents the systole of the atria, the QRS wave represents the systole of ventricles, and T wave represents their repolarization. Modern ECG devices use digital signal processing to analyze the shape and the consistency of, and the durations between these waveforms.

The heart rate (HR) can be measured by calculating the number of QRS waves in a minute. The HR may be expressed as a minute rate or as beats per minute (bpm). The rate of a heart functioning in a normal manner is not a constant, and the variation of the rate, which is commonly called the heart rate variability (HRV), has become one of the widely used markers for indicating the cardiac condition of a patient.

The ECG signal is thus analyzed for detecting various heart disorders, such as abnormalities in the heart rhythm, also termed arrhythmias. A common abnormal cardiac rhythm is the atrial fibrillation (AF). In the AF, the atria lose the nominal control pattern induced by the SA node. The contraction of the atria may start simultaneously in several points of the atria, spreading spuriously in the atria. Furthermore, the contraction is chaotic and the P waves disappear from the ECG signal. The contraction frequency of the atria during an AF episode is typically between 200 and 400/min. The AV node is not able to correct the lost sinus rhythm and the ventricular contractions are irregular. The ventricular beat-to-beat variation is high and can be seen as quick changes in the intervals between consecutive QRS complexes of the ECG signal.

The risk of an AF episode increases with age, and the occurrence of AF episodes is common among elderly people. However, the AF is not an immediate life-threatening disease. Yet, if the AF episodes remain persistent or last long, the blood remains circulating in the atria and may start to congeal. The resulting small blood clots may find their way to the brain and develop a stroke. Thus it is necessary to diagnose the occurrence and duration of the AF episodes in order to initiate a treatment and to follow the outcome of the treatment.

According to the American Heart Association (AHA) the prevalence in the USA of the AF and atrial flutter is about 2,000,000, while the total annual mortality caused by the said heart abnormalities is about 67,000. The listed hospital discharges are close to 400,000 (AHA, Heart Disease and Stroke Statistics—2003 Update). Atrial arrhythmia represents more than 50% of all hospital discharges of all types of cardiac arrhythmias. In the year 2002, 2.1 billion USD was paid to Medicare beneficiaries in this disease group. About 70% of people with atrial fibrillation are between 65 and 85 years and about 15% of strokes occur in people with atrial fibrillation (AHA).

The treatment of atrial arrhythmia may require a cardioversion to return the heart to a normal rhythm. This is carried out by medication or defibrillation, and a pacemaker may also be used. In order to make the diagnosis and to monitor the outcome of the treatment in acute care, the ECG signal obtained from a bedside monitor is commonly utilized. An esophagus ECG may also be used, in which a specific electrode setting is placed into the patient's esophagus close to the heart. This measurement method may give a better signal than a normal ECG measurement for identifying the atrial contraction, i.e. the P waves. This, in turn, may ease the rhythm diagnosis.

To maintain the sinus rhythm after the cardioversion, anti-arrhythmic medication may be used. However, this may cause side-effects such as pro-longed QT duration, which may be life-threatening. This is one of the reasons why continuous ECG monitoring is a common procedure for hospitalized arrhythmia patients and a minimum requirement in acute care of such patients.

The ECG arrhythmia algorithms of the state-of-art bedside monitors and telemetry systems feature an extensive analysis of ventricular beats, but not atrial analysis. The ECG algorithms nominally label the atrial arrhythmia or related atrial disorders for example by "Irregular Rhythm", which is not an exact diagnostic statement in the way "Atrial Fibrillation" would be. Therefore, such algorithms are not useful in acute care where the occurrence and recurrence of AF episodes should be monitored.

Although the current bedside monitors do not feature atrial analysis, methods and devices have been disclosed for detection of atrial fibrillation. These methods are, however, diagnosis tools which aim to classify the type of the AF and to give information for the selection of the most appropriate treatment. Thus their usage in acute care is limited. Such methods are disclosed in U.S. Pat. No. 6,178,347 (Olsson) or in U.S. Pat. No. 6,064,906 (Langberg et al.). In these methods, the ventricular component, i.e. the QRS wave, is removed from the ECG signal and a frequency analysis of the remaining signal, indicative of the atrial activity, is performed for classifying the type of atrial fibrillation in order to produce a prognosis of the patient.

Given the high prevalence of atrial arrhythmia and the importance of the prompt initiation and continuous monitoring of the treatment, the need for an automatic and precise diagnosis of atrial arrhythmia is therefore evident in acute care. The present invention seeks to provide a mechanism for this purpose.

SUMMARY OF THE INVENTION

The present invention seeks to bring about a new solution for reliably detecting atrial arrhythmia, such as atrial fibrillation, in acute care. The present invention also seeks to bring about a mechanism that allows the nursing staff to diagnose the occurrence and recurrence of AF episodes in order to initiate a proper treatment and to follow the outcome of the treatment.

In the present invention, a plurality of short-term HRV data sets, which overlap in time domain, are generated from the ECG signal. Frequency analyses are performed for the individual data sets for detecting whether the power spectral density of a data set includes at least one feature characteristic to a patient having an atrial arrhythmia episode. Based on the frequency analyses performed on the data sets, the occurrence of the heart's atrial arrhythmia episodes is evaluated.

Thus one aspect of the invention is providing a method for detecting atrial arrhythmia for an individual patient. The method includes the steps of receiving at least one electrical signal indicative of a heart's activity and generating, based on the at least one electrical signal, a plurality of short-term HRV data sets, one short-term HRV data set indicating the heart's rate variability within a time period of a given length and two consecutive short-term HRV data sets having a given time difference. The method further includes performing a frequency analysis of at least some of the short-term HRV data sets generated; defining, based on a single frequency analysis performed, a power level that corresponds to at least one selected frequency component in the corresponding short-term HRV data set, wherein a power level is defined for at least some of the short-term HRV data sets; and estimating, based on the power levels defined, an occurrence of the heart's atrial arrhythmia episodes. As discussed below, the term "frequency component" here refers to a frequency band or to a discrete frequency.

The invention provides a mechanism that reliably detects AF episodes and allows the clinical and nursing staff to be informed of the occurrence and recurrence of the episodes. A further advantage of the invention is that arrhythmia episodes may be detected almost in real-time, which allows an alarm of an onset to be given in the middle of the measurement process.

Another aspect of the invention is that of providing a system for detecting atrial arrhythmia for an individual patient. The system includes measurement means for obtaining data indicative of a heart's activity and first processing means for generating a first plurality of short-term HRV data sets from the data, one short-term HRV data set indicating the heart's rate variability within a time period of a given length. The system also includes frequency analysis means for performing a frequency analysis of at least some of the short-term HRV data sets, the frequency analysis means being configured to define a power level corresponding to at least one selected frequency component in an individual short-term HRV data set for obtaining a second plurality of power levels; and calculation means, responsive to the frequency analysis means, for estimating, based on the second plurality of power levels, an occurrence of the heart's atrial arrhythmia episodes.

Other features and advantages of the invention will become apparent by reference to the following detailed description and accompanying drawings.

BRIEF DESCRIPTION OF THE DRAWINGS

In the following, the invention and many of its embodiments are described more closely with reference to the examples shown in FIG. 2 to 10 in the appended drawings, wherein.

DETAILED DESCRIPTION OF THE INVENTION

In the present invention, known spectral characteristics of short-term HRV recordings are utilized for detecting AF episodes. This is first discussed with reference to FIGS. 2 and 3. The term short-term here refers to a recording lasting typically a few minutes. The length of the recording is typically between 2 and 5 minutes: The length is typically kept constant once selected, but it may also be changed during the measurement.

Figure 1:
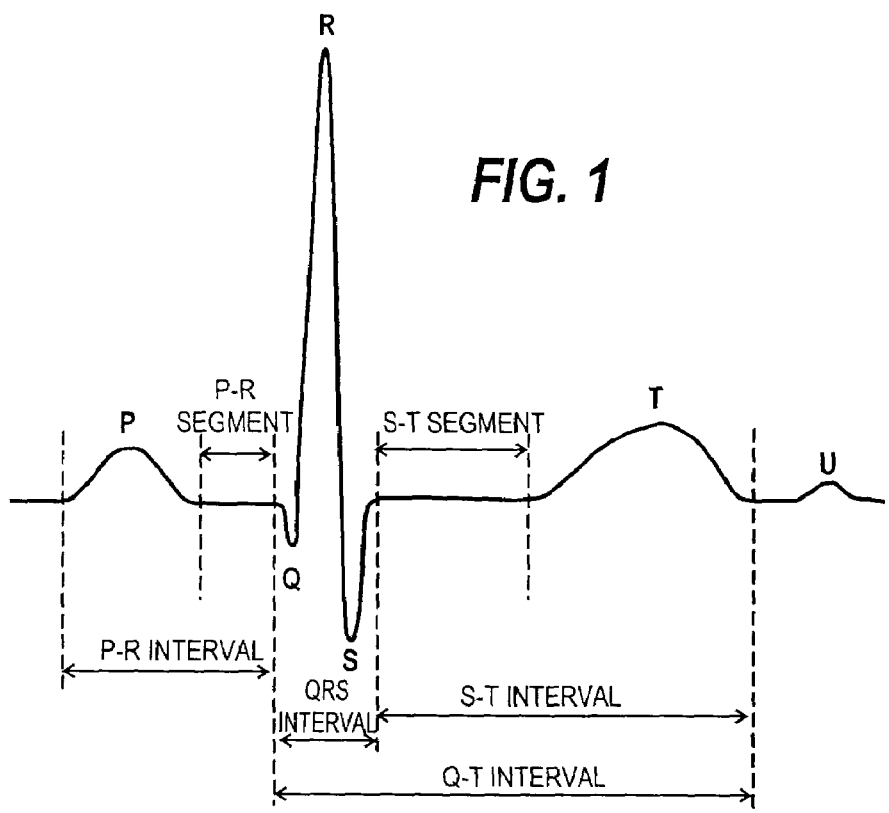
FIG. 1 illustrates an ECG signal of one cardiac cycle.
Figure 2:
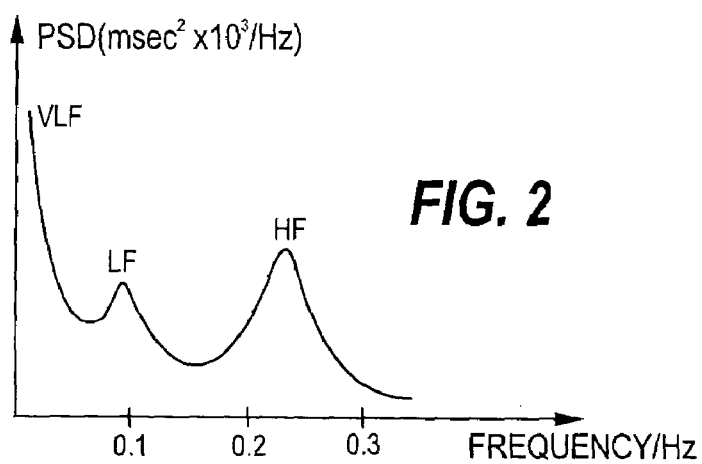
FIG. 2 is a graph illustrating a typical power spectral density obtained on the basis of a short-term HRV data set measured from a healthy person.
Figure 3:
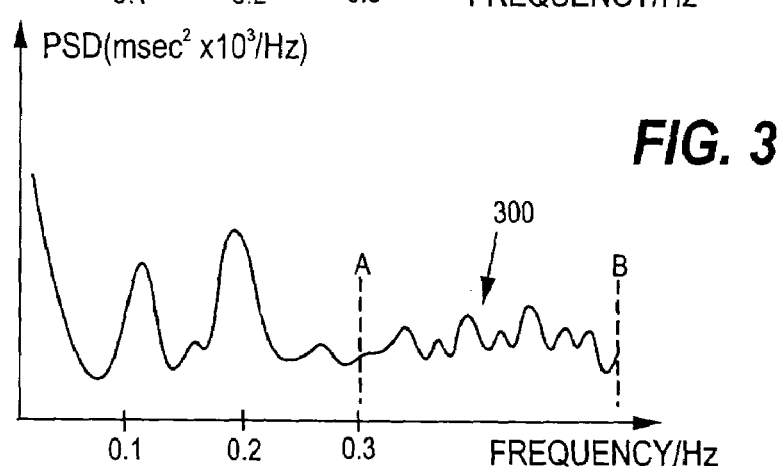
FIG. 3 is a graph illustrating a typical power spectral density obtained on the basis of a short-term HRV data set measured from a patient suffering from an AF episode.

FIG. 2 illustrates the results of a power spectral density analysis of a short-term HRV data set recorded from a healthy person. As can be seen, the power of a HRV signal is distributed around three main components, which are termed the very low frequency (VLF) component, the low frequency (LF) component, and the high frequency (HF) component. When the same measurement is performed on a patient suffering from an AF episode, the power distribution changes as is shown in FIG. 3. Besides that the three main peaks may now be less distinguishable, a major change is that the graph now shows a significant tail part 300 which resembles white noise. In order to distinguish the tail part from the three main components shown in FIG. 2, it is called the very high frequency (VHF) band below. In other words, a significant part of the signal power now lies on higher frequencies where no or negligible power exists in the case of a healthy person (cf. FIG. 2). The disturbance resembling white noise appears on the entire band, but it is more easily distinguishable on the higher frequencies where there are no major frequency components due to the normal operation of the heart.

The above-described spectral characteristics of short-term HRV recordings are utilized in the present invention for detecting the occurrence of AF episodes and for evaluating the onset and ending moments of the episodes. As discussed below, this involves evaluating the power level corresponding to a selected frequency band or a selected frequency, for example.

Figure 4:
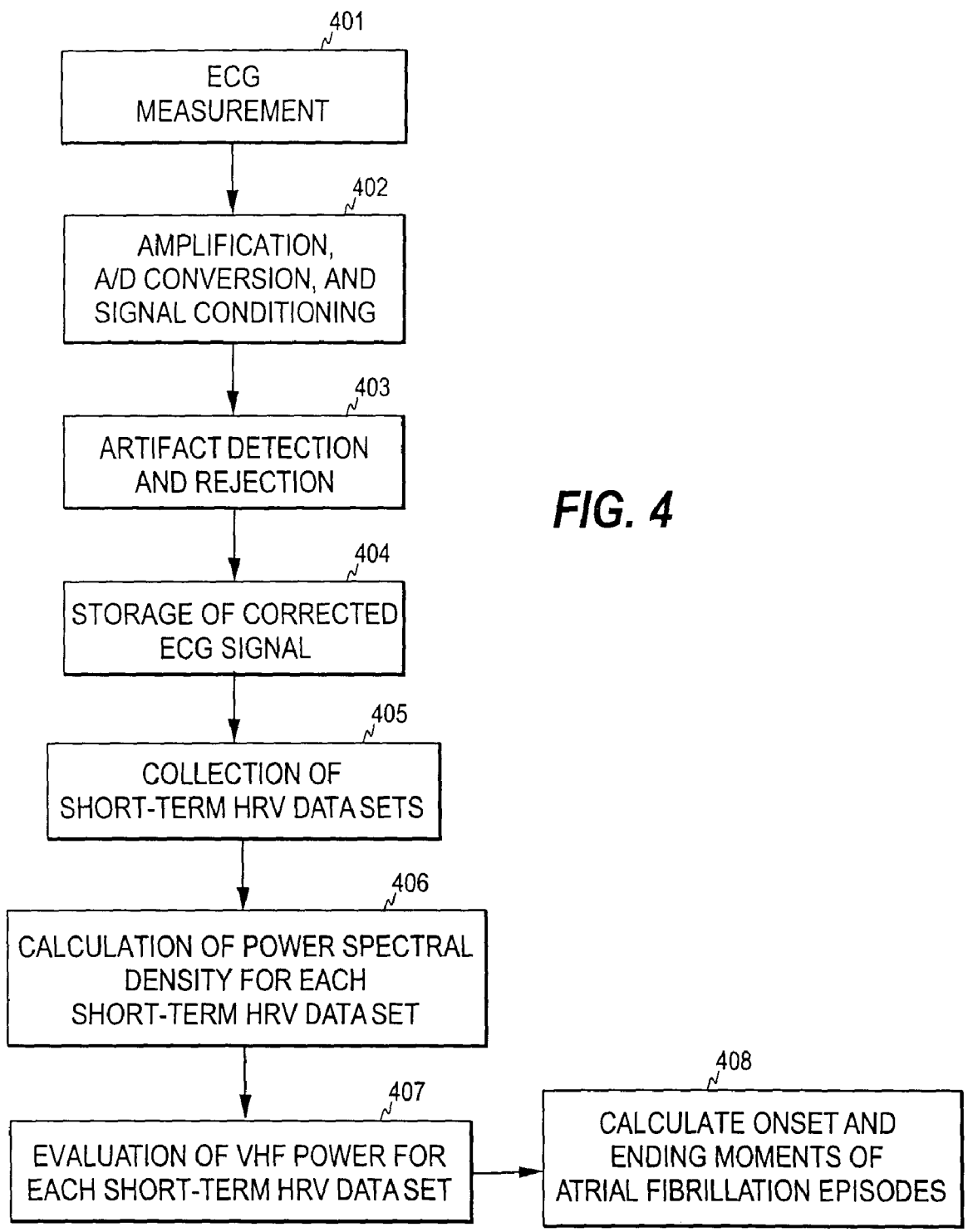
FIG. 4 is a flow diagram illustrating one embodiment of the method of the invention.

FIG. 4 illustrates one embodiment of the method of the invention. As normally in an ECG measurement, the signal received from the ECG sensor(s) is first supplied to an amplifier stage, which amplifies the signal before it is sampled and converted into digitized format in an A/D converter. The sampled signal is then buffered and processed in a digital signal processing unit. The processing unit may further perform the removal of the artifacts, thereby outputting a corrected ECG signal, i.e. the original ECG signal from which the artifacts have been removed. The above measures are taken in steps 401 to 403 shown in FIG. 4. The corrected ECG data is then stored (step 404) for further processing. The stored data includes the time moments corresponding to each sample in order to enable the reconstruction of the original signal.

Figure 5:
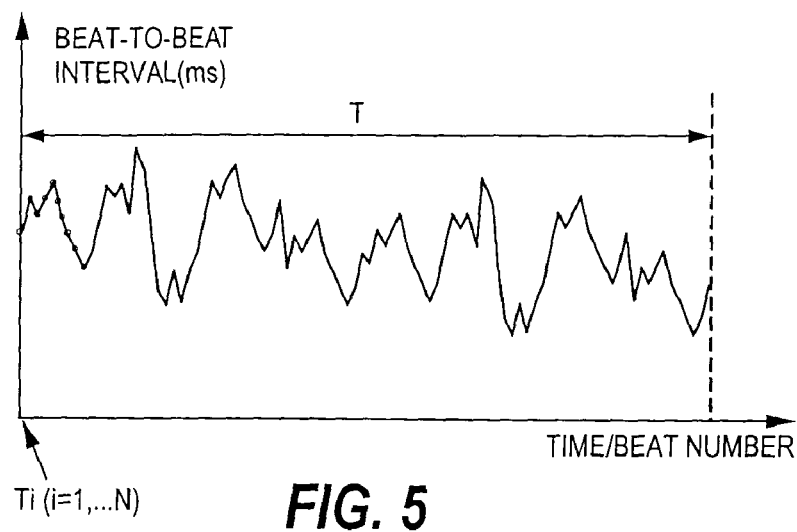
FIG. 5 illustrates one short-term HRV data set measured from the ECG signal.

In the next step (405), a plurality of short-term HRV data sets are collected from the stored ECG signal. FIG. 5 is a graph illustrating an example of one short-term HRV data set collected. The data set indicates the heart rate variability, i.e. the variation in the beat-to-beat intervals, as a function of time within a short time period T. The variation is typically measured in milliseconds. For determining the HRV data, the QRS complexes are identified from the ECG signal and the lengths of the consecutive R—R intervals are determined. As mentioned above, the length of the time period T is typically between 2 to 5 minutes, for example 3 minutes. Instead of a certain time period, the measurement may also cover a predetermined number of beats, such as 256 beats, which yields a similar amount of R—R interval data as a measurement covering a certain time period T.

Figure 6:
FIG. 6 is a time line illustrating the starting moments for measuring a plurality of HRV data sets within a selected short-term period.

FIG. 6 is a time line illustrating the measurement of said plurality of short-term HRV data sets. In the figure, Ti (i=1, 2, . . . N) indicates the starting moment of each of the measurements for determining one short-term HRV data set. In one embodiment of the invention, the time interval $\Delta T$ between the starting moments of two consecutive measurements is a constant that is rather small as compared to the measurement period T. In other words, the measurements overlap in time domain. If the length of the time period T is, say, 5 minutes, the time interval $\Delta T$ may be 10 seconds or 20 seconds, for example. Assuming that the time interval between two consecutive starting moments is 15 seconds, 20 short-term HRV data sets are then determined in 5 minutes. Respectively, if each measurement covers a predetermined number of beats, such as 256 beats, the difference between two consecutive measurements may correspond to a fixed number of beats, such as 16 beats.

With reference to FIG. 4 again, when the said plurality of short-term HRV data sets have been collected at step 405, a power spectral analysis is performed on each of the HRV data sets (406), i.e. the spectral distribution similar to those shown in FIGS. 2 and 3 is determined for each data set. This may be implemented, for example, by performing a Fourier transformation on each short-term HRV data set.

When the power spectral density analysis has been performed for each data set, a power level associated with each data set is evaluated (step 407) and the possible onset and ending moments of the AF episodes are approximated on the basis of the evaluations (step 408). In this embodiment of the invention, the evaluation of the power level refers to the evaluation of the amount of energy or power corresponding to the VHF band, a selected sub-band of the VHF band, or a selected VHF frequency. For example, the power level corresponding to the sub-band between reference marks A and B in FIG. 3 could be evaluated. This sub-band may be between 0.3 and 4 Hz, for example. The power level values used may be absolute values, normalized values, or relative values, and the power falling on a selected band may be evaluated by integrating the PSD in the said band, for example. The term power level thus here refers to any variable indicative of the absolute or relative amount of signal power or energy.

In this way, each data set yields a power or energy level which indicates the level of power or energy falling on a selected band or corresponding to a certain frequency.

Figure 7:
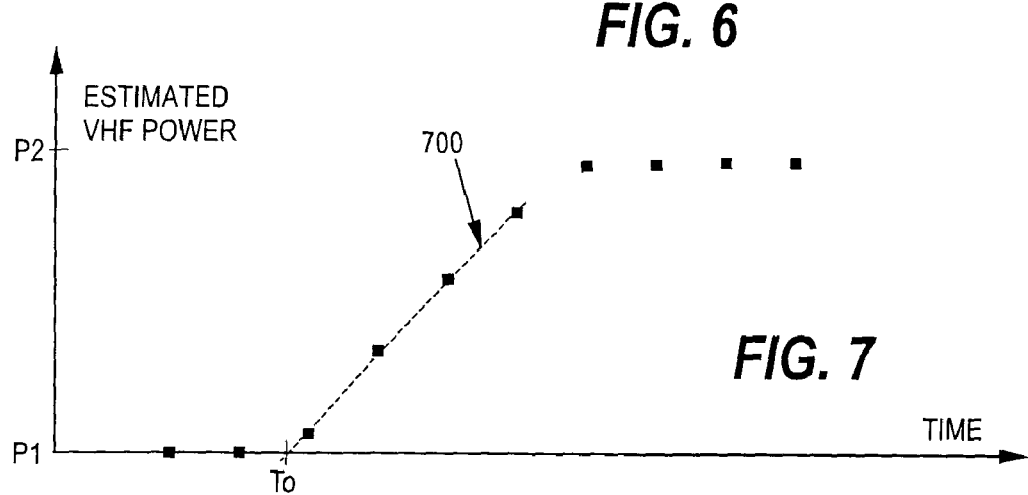
FIG. 7 illustrates the evaluation of an onset moment of an AF episode.
Figure 8:
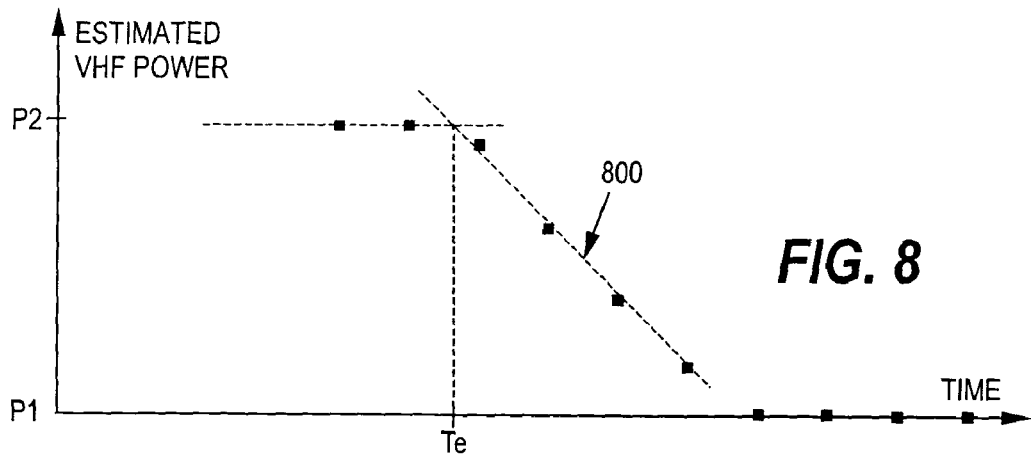
FIG. 8 illustrates the evaluation of an ending moment of an AF episode.

The estimated power values are then utilized as shown in FIGS. 7 and 8 for determining whether any onset or ending moments are within the measurement period. FIG. 7 illustrates the detection of an onset moment, while FIG. 8 illustrates the detection of an ending moment of an AF episode. Each square in the figures represents the power level obtained from the PSD analysis of the corresponding short-term HRV data set, i.e. one power level value is obtained for each data set. As discussed above, the power of the VHF band is higher during an AF episode, i.e. during the AF episodes the VHF power remains at a higher level than during a normal situation. When the measured power values of the short-term HRV data sets are presented as a function of time, as shown in FIGS. 7 and 8, the onset and ending moments To and Te, respectively, of the AF episodes can be interpolated by examining the change between a first power level P1 representing a normal situation and a second power level P2 representing an AF episode. When an AF episode starts, the power levels form an upward curve reaching plateau when the length of the AF episode reaches the length of the time period T of each HRV data set. Respectively, when an AF episode ends, the power levels will form a downward curve reaching plateau when the time elapsed from the ending moment Te reaches the length of the time period T of each HRV data set. The onset and ending moments may be defined by linearly approximating the upward and downward curves. The estimated onset moment To then corresponds to the point where a line 700 approximating said upward curve intersects with the first power level P1. Respectively, the estimated ending moment corresponds to the point where a line 800 approximating said downward curve intersects with the second power level P2.

In the above embodiment, the power levels of one VHF band or frequency were monitored. Although the onset of an AF episode is probably most reliably detectable by monitoring the power level corresponding to a given VHF band or to a given VHF frequency in the power spectrum of a short-term HRV data set, the lower part of the spectrum, i.e. the VLF/LF/HF frequencies, may also be utilized. Furthermore, it is possible to utilize more than one band or frequency belonging to either, i.e. upper or lower, part of the spectrum. For example, it is possible to divide the selected band into sub-bands and to measure the power level of one or more selected sub-bands, such as the power level of one or more bands belonging to the tail part 300. Since the power level increases within the entire tail part during an AF episode, the onset of an episode can be detected from various parts of the tail part. However, depending on the type of the fibrillation, some parts of the tail part may indicate the power level increase quicker than the other parts. Furthermore, the power levels corresponding to one or more VLF/LF/HF bands or to one or more VLF/LF/HF frequencies may be utilized alone or in combination with the power levels corresponding to one or more VHF bands or to one or more VHF frequencies. For example, two frequencies might be selected from the VLF/LF/HF band. If the power levels of two or more bands/frequencies are monitored, the final power level representing the corresponding short-term HRV data set may be obtained as the average of the power levels or as the ratio of the power levels at two different bands/frequencies, for example. The ratio of the VHF power to the VLF/LF/HF power may also be used. In a normal situation of FIG. 2, this ratio is very small, but shows increased values during AF episodes.

It is to be noted here that even though the steps of the method are shown as consecutive steps in FIG. 4, they may be performed in parallel. In other words, new short-term HRV data sets may be collected continuously, while the data sets already collected are being processed.

Since a new measurement result is obtained at time intervals of $\Delta T$ (assuming that the first measurement period T has already been passed) and since the onset of an episode can be detected already when the power level begins to change, the method of the invention offers almost a real-time method for detecting AF episodes. Therefore, an alarm of the onset of an episode may be given promptly even if the actual measurement still continues. The more latency is allowed, the more accurate is the approximation of the onset and ending moments, since the accuracy of the approximation improves with an increasing number of power levels defined. Once the slope of the power curve is measured during an AF episode, the process can be speeded up by estimating the onset and ending moments of subsequent AF episodes by means of that slope, i.e. the measured slope is used as a reference slope for speeding up the calculation at subsequent episodes.

In the above embodiments of the invention, time interval $\Delta T$ was kept constant during the measurement. In another embodiment of the invention, the said time interval is changed to optimize the calculation power needed during the monitoring. During normal circumstances, i.e. when there is no indication of an AF episode, the time interval between two consecutive HRV data sets may be rather long, such as one minute. However, when an ongoing measurement indicates that there might be an onset of an AF episode, the time interval may be shortened in order to examine that part of the signal more accurately. Since the signal is stored in a memory, the calculation process may return backwards in time domain when detecting the onset of an AF episode, and start to calculate the HRV data sets with a shorter time interval $\Delta T$, beginning from a moment just prior to the estimated onset moment. The shorter time interval $\Delta T$ may be maintained as long as the AF episode lasts, for example.

Furthermore, it is not necessary to utilize each short-term HRV data set, but the calculation power needed may be decreased by performing the frequency analysis for only part of the data sets. For example, during normal circumstances the frequency analyses may be performed less frequently just to check whether the situation of the patient remains unchanged. If a change is detected, the time interval $\Delta T$ may be shortened and a frequency analysis may be performed for each short-term HRV data set generated.

Figure 9:
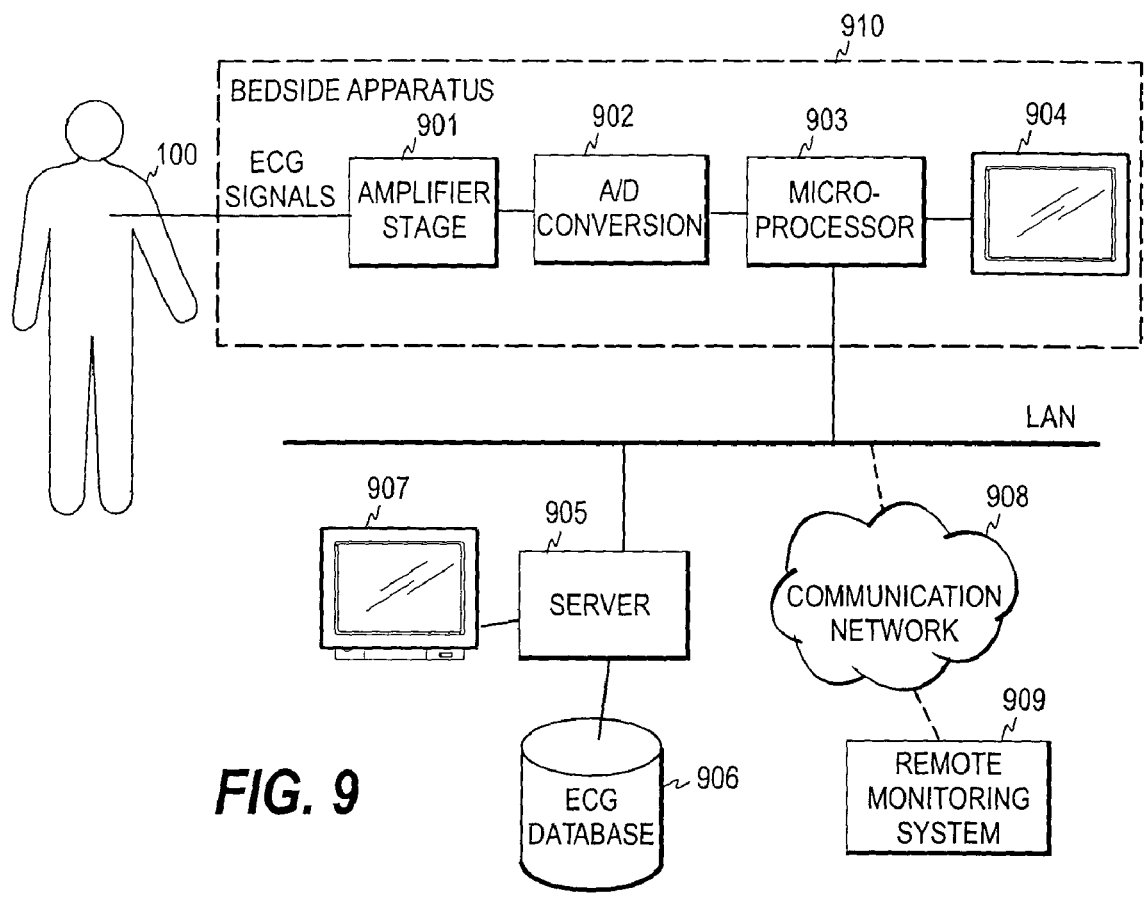
FIG. 9 illustrates one embodiment of the system of the invention in a hospital environment.

FIG. 9 illustrates one embodiment of the system according to the invention, in which a centralized server may serve one or more bedside monitors 910. The ECG signals obtained from the different sensors attached to a patient 100 are supplied to an amplifier stage 901, which amplifies the signals before they are sampled and converted into digitized format in an A/D converter 902. The digitized signals are supplied to a microprocessor 903 which may then carry out the detection and rejection of artifacts. The microprocessor may further be provided with a monitor 904 for displaying the ECG signal and the results of the AF detection at the patient.

The microprocessor is further connected to a local area network (LAN) of the hospital for transferring the ECG signal data of a patient to a centralized server 905. The server is provided with a database 906 holding the ECG signal data received from one or more bedside monitors 910. The centralized server performs steps 404 to 408 shown in FIG. 8, i.e. the server performs the above-described analysis in order to detect the AF episodes. A remote monitoring system 909 may further be connected to the LAN through a communication network 908 in order to monitor the results from a remote location. The remote monitoring system may also include one or more bedside monitors that send their ECG data to the centralized server for detecting the AF episodes of a patient at a remote location.

Figure 10:
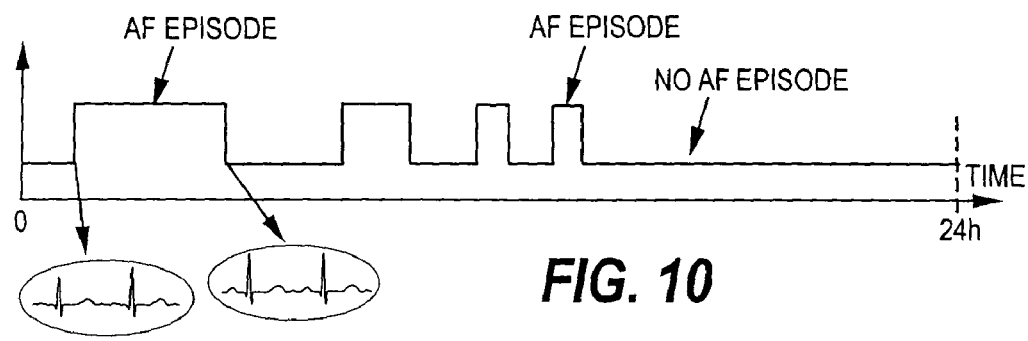
FIG. 10 is a graph illustrating an example of the detected AF episodes over a twenty-four hour cycle.

If the measurement is performed continuously for a longer period, such as for one day, the estimated onset and ending moments can be presented over that period. FIG. 10 illustrates an example of a graph showing the onset and ending moments, as well as the lengths of the AF episodes, over a period of 24 hours. As the server database further includes the corresponding ECG signal data, the ECG signal corresponding to these significant moments may also be displayed to the nursing staff, as shown by the ovals in FIG. 10. By presenting the AF episodes and their durations over a longer period, such as 24 hours, the nursing staff may efficiently evaluate the outcome of the treatment given to the patient. By illustrating the ECG curve at the onset and ending moments, further valuable information may be obtained about the reasons triggering the AF episodes.

Although the invention was described above with reference to the examples shown in the appended drawings, it is obvious that the invention is not limited to these, but may be modified by those skilled in the art without departing from the scope and spirit of the invention. For example, the measurement devices by which the ECG data is obtained from the patient may include various types of known devices or measurement methods. It is not even necessary to measure the ECG of the patient, but the short-term HRV data sets may be calculated based on pulse measurement or invasive pressure monitoring, for example. The HRV data sets do not necessarily have to overlap in time domain, but the next one may begin when the previous one ends, for example. However, in this case the accuracy of the approximation of the onset and ending moments will decrease. Regarding the power levels obtained from the spectral analyses, it is not necessary to evaluate the onset and ending moments but the power levels may also be utilized in various ways. For example, the power levels may be used to evaluate the proportion of the AF episodes.

The invention claimed is:

1. A method for detecting atrial arrhythmia for a patient, the method comprising the steps of:
   receiving at least one electrical signal indicative of a heart's activity;
   based on the at least one electrical signal, generating a plurality of short-term HRV data sets, a short-term HRV data set indicating the heart's rate variability within a time period of a given length, two consecutive short-term HRV data sets having a given time difference;
   performing a frequency analysis of at least some of the generated short-term HRV data sets;
   based on a performed frequency analysis, defining a power level that corresponds to at least one selected frequency component in the corresponding short-term HRV data set, wherein a power level is defined for at least some of the short-term HRV data sets; and based on the power levels so defined, ascertaining an occurrence of an atrial arrhythmia episode of the heart.

2. A method according to claim 1, wherein the ascertaining step includes determining onset and ending moments of an atrial arrhythmia episode of the heart.

3. A method according to claim 1, wherein the performing step includes performing a frequency analysis of all generated short-term HRV data sets and the defining step includes defining a power level for all generated short-term HRV data sets.

4. A method according to claim 1, wherein the performing step includes performing a Fourier transformation on at least some of the short-term HRV data sets.

5. A method according to claim 1, wherein the given length is between 2 and 5 minutes.

6. A method according to claim 5, wherein the given time difference is substantially shorter than said time period.

7. A method according to claim 6, wherein the given time difference is between 10 and 30 seconds.

8. A method according to claim 6, wherein the given time difference remains constant for all short-term HRV data sets generated.

9. A method according to claim 6, further comprising a step of giving the time difference a new value during the generating step.

10. A method according to claim 9, further comprising a step of replacing some of the generated short-term HRV data sets by generating new short-term HRV data sets beginning from a selected time moment, wherein the time difference between two consecutive new short-term HRV data sets has said new value.

11. A method according to claim 1, wherein the at least one selected frequency component is above 0.3 Hz.

12. A method according to claim 11, wherein the at least one selected frequency component forms at least one frequency band.

13. A method according to claim 1, wherein the least one selected frequency component is below 0.3 Hz.

14. A method according to claim 1, wherein the plurality of short-term HRV data sets covers a desired monitoring period.

15. A method according to claim 14, wherein the desired monitoring period is 24 hours.

16. A system for detecting atrial arrhythmia for a patient, the system comprising:

measurement means for obtaining data indicative of a heart's activity;

processing means for generating a plurality of short-term HRV data sets from the data, a short-term HRV data set indicating the heart's rate variability within a time period of a given length;

frequency analysis means for performing a frequency analysis of at least some of the short-term HRV data sets, the frequency analysis means being configured to define a power level corresponding to at least one selected frequency component in an individual short-term HRV data set for obtaining a plurality of power levels; and calculation means, responsive to the frequency analysis means, for ascertaining, based on the plurality of power levels, an occurrence of an atrial arrhythmia episode of the heart.

17. A system according to claim 16, wherein the calculation means is configured to determine onset and ending moments of an atrial arrhythmia episode of the heart.

18. A system according to claim 16, wherein the frequency analysis means is configured to define a power level corresponding to a selected frequency band in an individual short-term HRV data set.

19. A system according to claim 16, further comprising means for displaying the atrial arrhythmia episodes and their durations in time domain.

20. A method according to claim 1 wherein the given time difference is substantially shorter than said time period.

21. A method according to claim 20 wherein the given time difference remains constant for all short-term HRV data sets generated.

22. A method according to claim 20 further comprising a step of giving the time difference a new value during the generating step.

23. A method according to claim 22 further comprising a step of replacing some of the generated short-term HRV data sets by generating new short-term HRV data sets beginning from a selected time moment, wherein the time difference between two consecutive new short-term HRV data sets has said new value.

24. A system according to claim 16 where said frequency analysis means performs a Fourier transformation on at least some of the short-term HRV data sets.

* * * * *